(12) United States Patent
Cheim et al.

(10) Patent No.: US 11,631,533 B2
(45) Date of Patent: Apr. 18, 2023

(54) SYSTEM FOR SENSOR UTILIZATION IN A TRANSFORMER COOLING CIRCUIT

(71) Applicant: HITACHI ENERGY SWITZERLAND AG, Baden (CH)

(72) Inventors: Luiz Cheim, Raleigh, NC (US); Pierre Lorin, Savièse (CH)

(*) Notice: Subject to any disclaimer, the term of this patent is extended or adjusted under 35 U.S.C. 154(b) by 381 days.

(21) Appl. No.: 16/958,804

(22) PCT Filed: Dec. 31, 2018

(86) PCT No.: PCT/US2018/068143
§ 371 (c)(1),
(2) Date: Jun. 29, 2020

(87) PCT Pub. No.: WO2019/133972
PCT Pub. Date: Jul. 4, 2019

(65) Prior Publication Data
US 2021/0065970 A1    Mar. 4, 2021

Related U.S. Application Data

(60) Provisional application No. 62/612,377, filed on Dec. 30, 2017.

(51) Int. Cl.
*H01F 27/10* (2006.01)
*H01F 27/40* (2006.01)
(Continued)

(52) U.S. Cl.
CPC .......... *H01F 27/402* (2013.01); *G01K 13/00* (2013.01); *G01N 33/2841* (2013.01);
(Continued)

(58) Field of Classification Search
CPC ........ H01F 27/402; H01F 27/02; H01F 27/10; H01F 27/28; H01F 2027/404;
(Continued)

(56) References Cited

U.S. PATENT DOCUMENTS 4,337,820 A * 7/1982 Pierce ................. F28D 15/0266
340/646
6,401,518 B1 6/2002 O'Keeffe et al.
(Continued)

FOREIGN PATENT DOCUMENTS

| CN | 1416580 A | 5/2003 |
| CN | 1588587 A | 3/2005 |

(Continued)

OTHER PUBLICATIONS

International Search Report and Written Opinion of the International Searching Authority, PCT/US2018/068143, dated May 3, 2019, '12 pages.

(Continued)

*Primary Examiner* — Tuyen T Nguyen
(74) *Attorney, Agent, or Firm* — Sage Patent Group (57) ABSTRACT

A transformer includes a tank with an insulating fluid, a radiator for cooling the insulating fluid, and one or more sensors arranged to measure insulating fluid properties in a location where the insulating fluid has a lower temperature.

15 Claims, 8 Drawing Sheets

(51) Int. Cl.
  *G01K 13/00*   (2021.01)
  *G01N 33/28*   (2006.01)
  *H01F 27/02*   (2006.01)
  *H01F 27/28*   (2006.01)

(52) U.S. Cl.
  CPC ......... *G01N 33/2847* (2013.01); *H01F 27/02* (2013.01); *H01F 27/10* (2013.01); *H01F 27/28* (2013.01)

(58) Field of Classification Search
  CPC .... H01F 27/12; G01K 13/00; G01N 33/2841; G01N 33/2847
  See application file for complete search history.

(56) References Cited

U.S. PATENT DOCUMENTS

| | | | | |
|---|---|---|---|---|
| 8,081,054 B2* | 12/2011 | Guentert, III | ........... | H01F 27/12 336/58 |
| 11,322,289 B2* | 5/2022 | Findeisen | ............. | H01F 27/402 |
| 2011/0140820 A1 | 6/2011 | Guentert et al. | | |
| 2017/0168034 A1 | 6/2017 | Fenton | | |

FOREIGN PATENT DOCUMENTS

| | | |
|---|---|---|
| CN | 201054295 Y | 4/2008 |
| CN | 101308189 A | 11/2008 |
| CN | 202364102 U | 8/2012 |
| CN | 102709037 A | 10/2012 |
| CN | 202713874 U | 1/2013 |
| CN | 103928216 A | 7/2014 |
| CN | 104465027 A | 3/2015 |
| CN | 105934806 A | 9/2016 |
| CN | 106872864 A | 6/2017 |
| CN | 106920642 A | 7/2017 |
| CN | 1319237 A | 10/2021 |
| EP | 2899728 A1 | 7/2015 |
| GB | 2153597 A | 8/1985 |
| JP | 03101112 A | 4/1991 |
| JP | 0369211 U | 7/1991 |
| JP | 11142079 A | 5/1999 |
| JP | 2003506863 A | 2/2003 |
| JP | 2006505760 A | 2/2006 |
| WO | WO-2012059503 A1 * | 5/2012 ............. G01K 13/00 |
| WO | 2017125407 A1 | 7/2017 |
| WO | 2017172703 A1 | 10/2017 |

OTHER PUBLICATIONS

Office Action for Japanese Patent Application No. 2020-536558, dated Jun. 1, 2021, 10 pages.

Decision to Grant for Japanese Patent Application No. 2020-536558, dated Sep. 14, 2021, 3 pages.

Office Action for Chinese Patent Application No. 201880084024.6, dated Sep. 21, 2022, 17 pages.

* cited by examiner

SYSTEM FOR SENSOR UTILIZATION IN A TRANSFORMER COOLING CIRCUIT

CROSS REFERENCE TO RELATED APPLICATIONS

This application is a 35 U.S.C. § 371 national stage application of PCT International Application No. PCT/US2018/068143 filed on Dec. 31, 2018, which in turns claims domestic priority to U.S. Provisional Patent Application No. 62/612,377, filed on Dec. 30, 2017, the disclosures and content of which are incorporated by reference herein in their entirety.

FIELD OF THE INVENTION

The present application is directed to a sensor that allows for monitoring of various properties of an insulating fluid of an in-operation transformer cooling circuit.

BACKGROUND

Transformer gas and moisture sensors typically require a pump system to circulate insulating fluid (such as dielectric fluid) internally and provide the fluid to the sensors for readings. The pump system ensures that new insulating fluid is continuously in circulation for contact with the sensor. These and other problems indicate a need in the art for a system that can measure properties of insulating fluid without requiring a pump to circulate the fluid, among other features.

SUMMARY

In one embodiment, a transformer includes a core, at least one coil winding, and insulating fluid disposed inside a tank. A radiator having cooling fins and a first conduit and a second conduit for transferring the insulating fluid between the transformer tank and radiator is provided. At least one of the first and second conduits has a port for measurement access to the insulating fluid therein and a sensor for measuring properties of the insulating fluid through the port.

In another embodiment, a transformer includes a core, at least one coil winding, and insulating fluid disposed inside a tank. A radiator having cooling fins and a first header and a second header for transferring the insulating fluid between the tank and the radiator is provided. At least one of the first and second headers has the port for measurement access to the insulating fluid therein and a sensor for measuring properties of the insulating fluid through the port.

Embodiments of the present application include methods, systems and apparatuses for measuring properties of a transformer insulating fluid. Embodiments of the present application also include methods, systems and apparatuses for sensing transformer fluid properties. Other embodiments include apparatuses, systems, devices, hardware, methods, and combinations for a transformer fluid sensor. Further embodiments, forms, features, aspects, benefits, and advantages of the present application shall become apparent from the description and figures provided herewith.

BRIEF DESCRIPTION OF THE DRAWINGS

In the accompanying drawings, structural embodiments are illustrated that, together with the detailed description provided below, describe exemplary embodiments of a sensor that is integrated with a transformer cooling system. One of ordinary skill in the art will appreciate that a component may be designed as multiple components or that multiple components may be designed as a single component.

Further, in the accompanying drawings and description that follow, like parts are indicated throughout the drawings and written description with the same reference numerals, respectively. The figures are not drawn to scale and the proportions of certain parts have been exaggerated for convenience of illustration.

DETAILED DESCRIPTION

Figure 1:
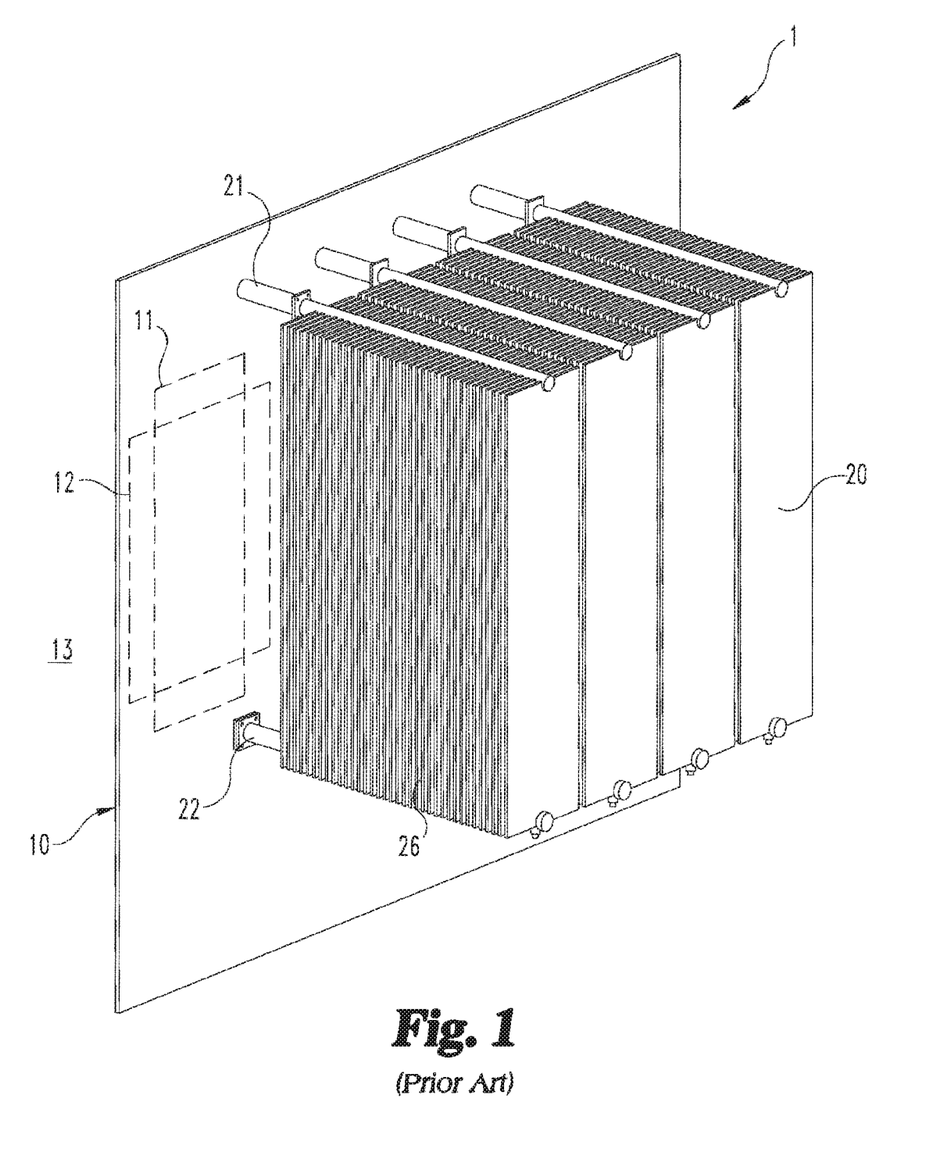
FIG. 1 depicts a prior art transformer cooling system in communication with a transformer tank.

With reference to FIG. 1, a transformer 1 is shown having an exemplary radiator 20 with first and second conduits 21, 22 connecting the radiator 20 to the tank 10 of transformer 1. The transformer 1 has a core 11, at least one coil winding 12, and insulating fluid 13 inside the tank 10. The exemplary radiator 20 has fins 26 and first and second conduits 21, 22 for transferring the insulating fluid to and from the transformer tank 10. Alternatively, the radiator 20 has fins formed of a tubular shape or the transformer is provided with a cooler, such as in a forced insulating fluid cooling system. It should be understood that the present disclosure and use of the term "radiator" contemplates any of the foregoing arrangements.

A radiator 20 is typically has fins 26 through which hot insulating fluid coming from the top of the tank 10 is cooled through natural circulation (ONAN) or forced circulation (ONAF/OFAF/ODAF). In certain embodiments, the cooling process is helped by the use of fans that blow air onto the fins or/and pumps that increase dielectric fluid velocity thus facilitating cooling.

As is well known, an insulating fluid such as dielectric fluid is transferred between the transformer 10 tank and the radiator 20 and heat is dissipated and transferred to the surrounding environment through the fins 26, so that the cooling fluid exiting the radiator 20 and entering the transformer tank 10 through the second conduit 22 is at a lower temperature than the insulating fluid that has entered the first conduit 21.

Figure 2:
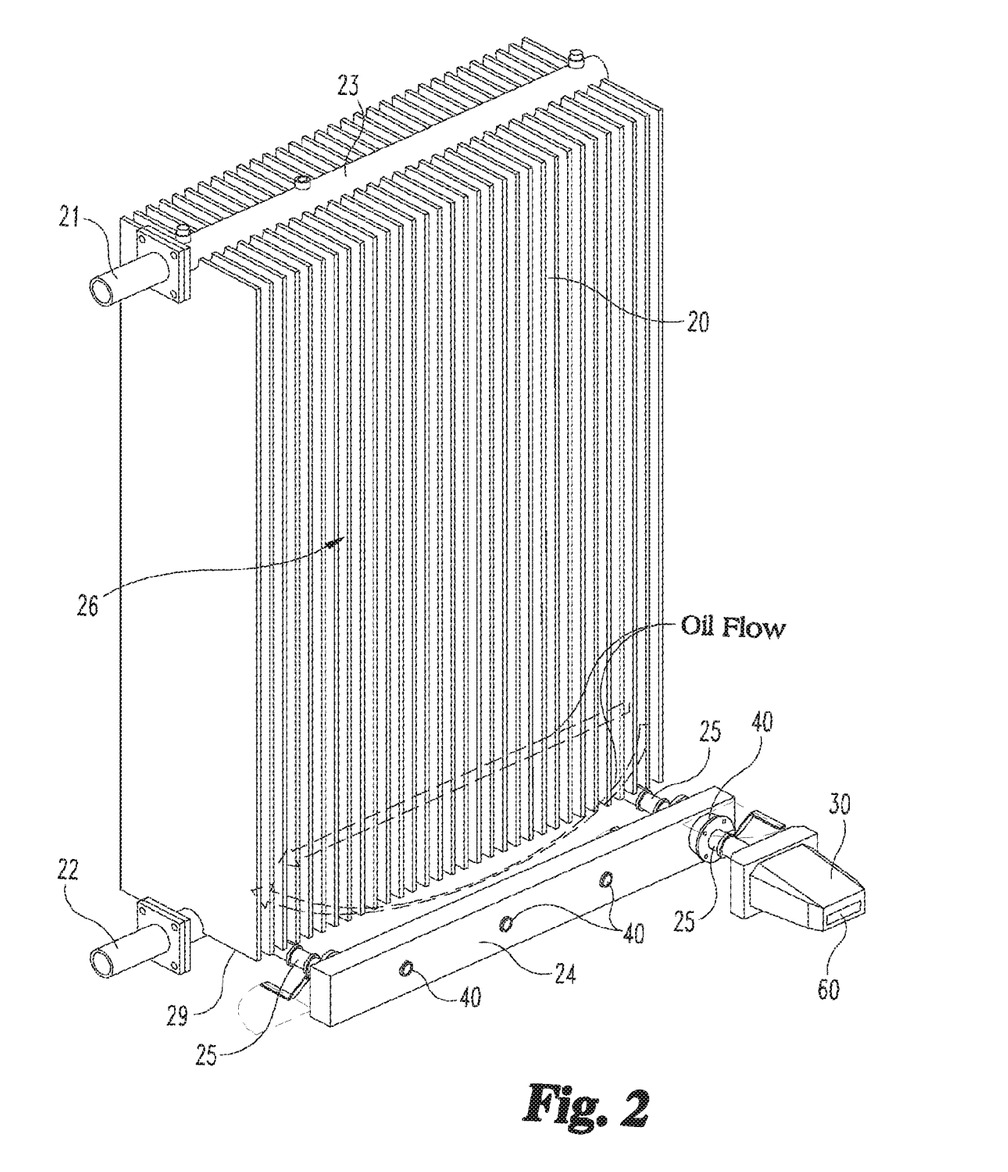
FIG. 2 depicts the transformer cooling system having an alternate insulating fluid flow path for a sensor and a sensor installed at the port thereof.

As shown in FIG. 2, for example, the placement of a sensor 30 according to the present disclosure is shown. Sensor 30 is placed proximate to the lower portion or bottom of the radiator 20, which allows the sensor 30 to have direct contact with circulating insulating fluid at lower temperatures as compared to the temperature of the insulating fluid at the top of the radiator 20.

First and second headers 23, 24 may be provided in connection with the respective first and second conduits 21, 22 and the radiator 20 for transferring insulating fluid between the cooling system and the transformer tank 10. The insulating fluid flows through first conduit 21 to first header 23 and through a first one of the valves 25, through radiator 20, and to second header 24 or sensor-carrying compartment after heat is dissipated and the insulating fluid is cooled. The insulating fluid flowing through the second header 24 is accessible to measurement by sensor 30 through the port 40 in the second header 24. The insulating fluid may be returned to second conduit 22 downstream of sensor 30. The properties of the insulating fluid may be measured by indirect means or by direct contact with the insulating fluid through the sensor 30. Other valves 25 may be provided at the downstream end of the second header 24, and also between the sensor 30 and the second header 24, as shown in FIG. 2, to facilitate installation and maintenance of the sensor 30.

By way of non-limiting example, the sensor 30 can be provided with a probe that is in direct contact with the insulating fluid. In one embodiment, the sensor 30 is an optical detector such as in a photoacoustic sensor for measuring sound at different wavelengths of light, or a FTIR (fourier-transform infrared) spectroscopic sensor, or a solid state sensor such as a metallic plate. Further, a membrane type sensor or any other type of technology that is capable of measuring properties of insulating fluid through the port 40 provided in a conduit 21, 22 and/or header 23, 24, 34 is contemplated by the present disclosure. Alternatively, the sensor 30 can be installed at or near the valve 25 or other fitting or as part of the header 24 or other circuit of the radiator 20. The sensor 30 may be provided with electronics, a power supply and other components for measuring one or more properties of the insulating fluid.

In one embodiment, the sensor 30 is a resistance temperature detector. Such a resistance temperature detector has a 2-wire, 3-wire, or 4-wire arrangement depending on the application. The sensor 30 provides a linear increase in resistance as the temperature rises. Still other types of sensors 30 are contemplated for measuring properties of the insulating fluid. Examples of such of such sensors are pressure, oil level and multi-gas detecting sensors. In another embodiment, the sensor 30 is the CoreSense™ sensor available from ABB Inc. that provides continuous online monitoring of gases in transformer insulating fluid, including hydrogen and moisture.

With continued reference to FIG. 2, the sensor 30 is installed at the header 24 that is near or below the bottom or base 29 of the radiator 20 as the insulating fluid temperature is lower at that location. The insulating fluid temperature at that measurement location will not impact the operation of the sensor 30 electronics.

The sensor 30 measures the temperature, dissolved gas and/or moisture characteristics of the insulating fluid. Measurement values include but are not limited to the presence and concentration of various dissolved gases and/or moisture and water in the insulating fluid. By way of non-limiting example, a dissolved gas sensor is provided for the detection of hydrogen gas dissolved in transformer insulating fluid, but may also detect carbon monoxide, carbon dioxide, acetylene, ethylene, methane and various other dissolved gases in transformer insulating fluid. Alternatively, a moisture sensor may be provided in connection with the port 40 to detect water in the transformer insulating fluid. An electronics and communication module 60 may be provided to drive the sensor functions for dissolved gas, moisture, and other measurements.

The sensor 30 does not require a pump in order to monitor new or continuous insulating fluid in contact therewith, as is required by many known sensors and measurement systems for transformer insulating fluid. Insulating fluid moves continuously from the transformer tank 10 through the first conduit 21, into the radiator 20 and exits the radiator 20 through the second conduit 22 back to the transformer 10 while passing through header 24. Therefore the present disclosure enables measuring the properties of the insulating fluid continuously. Such properties include the presence and concentration of constituents in the insulating fluid, dielectric loss, resistivity and particles in the insulating fluid. Other chemical and physical properties of the insulating fluid that may be measured are interfacial tension, power factor, dielectric strength, moisture content, oxidation inhibitor content, acidity, color and various other properties of insulating fluid.

Additionally, the first and second conduits 21, 22 may have one or more ports 40 located along the circumference thereof, which allows the insulating fluid to be measured by the sensor 30 directly as through a probe of the sensor 30 or indirectly, such as optically, acoustically through the port 40, or through contact with the port 40. In one embodiment, the port 40 is a window through which the optical or acoustic properties can be detected.

Figure 3A:
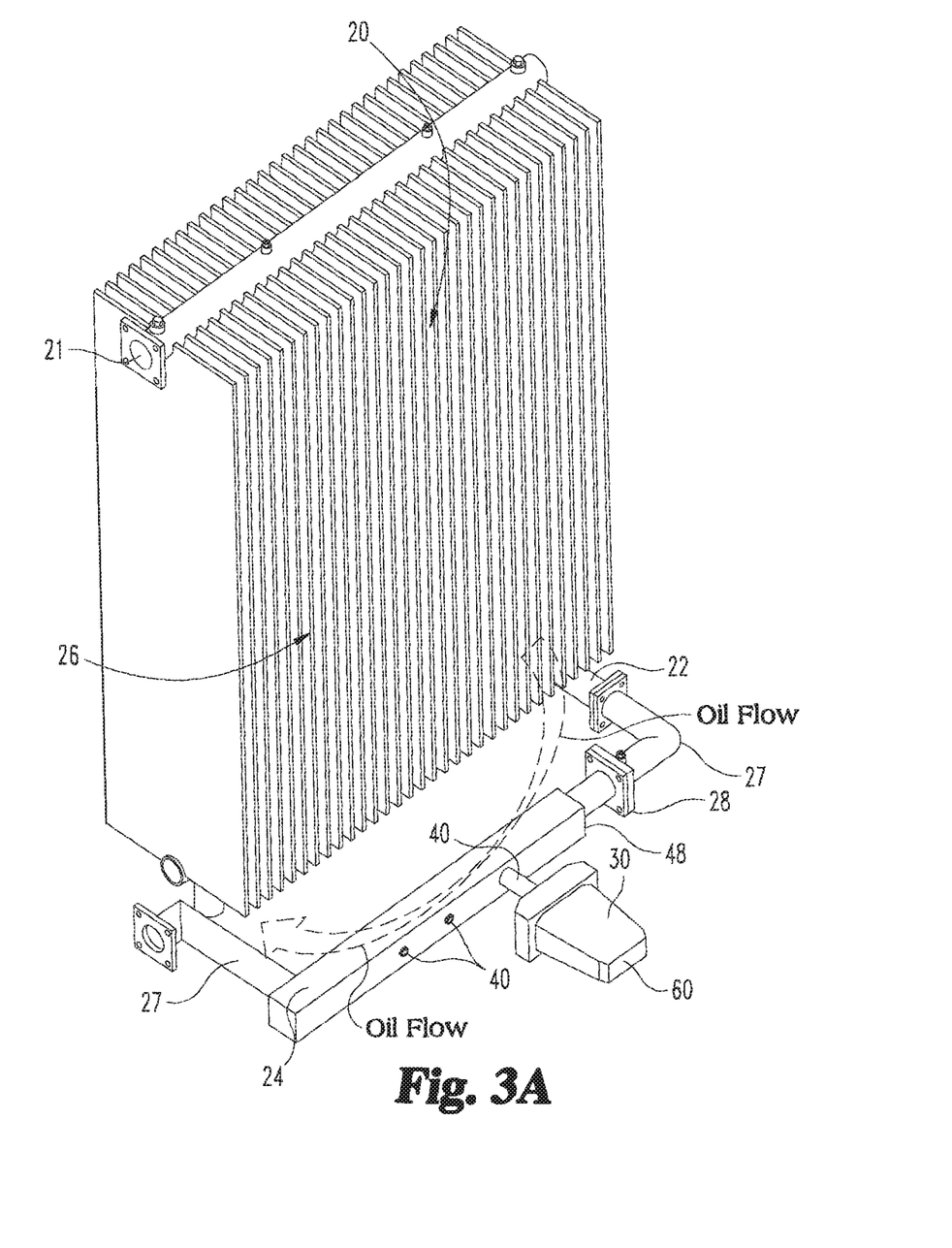
FIG. 3A depicts the transformer cooling system having the insulating fluid flow path directed through valves and a horizontally oriented header with the sensor installed in direct contact with insulating fluid flow through the header.

With reference now to FIG. 3A, a radiator 20 is shown having a second conduit 22 connected through a valve 28 to an upstream end 48 of a header 24 which is provided in a horizontal orientation and in-line with the insulating fluid flow. First and second bends 27 are provided in the header 24 for directing the insulating fluid flow around the fins 26 of the radiator 20 and bypassing the radiator 20 for return directly to the tank 10. The radiator fins 26 may be reduced in size in the area of the bend 27. However, the impact to the cooling system by reduction in surface area of the fins 26 is kept to a minimum by reducing the surface area of only a few fins 26. The shape of the header 24 is designed to allow free insulating fluid flow. One or more ports 40 are provided in the header 24 to allow measurement access by one or more sensors 30 for direct or indirect measurement of the insulating fluid.

Figure 3B:
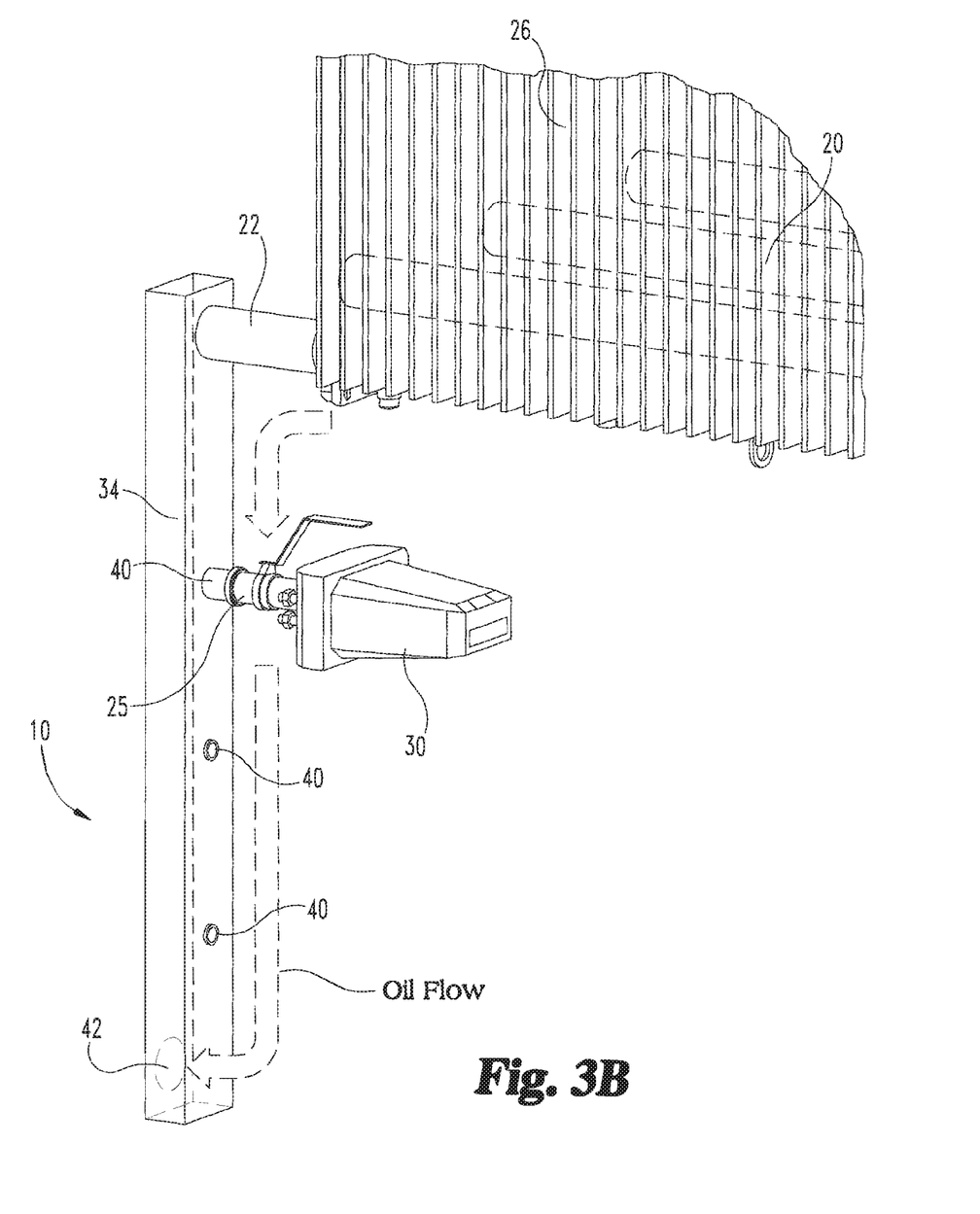
FIG. 3B depicts the transformer cooling system having the insulating fluid flow directed through a vertically oriented header with the sensor installed in monitoring contact between the radiator and the transformer tank.

Referring now to FIG. 3B, a radiator 20 is shown having a second conduit 22 connected to a header 34 which is mounted in a vertical orientation on the side of the transformer tank 10. The sensor 30 is provided in-line with the insulating fluid flow which is accessible through the port 40. The insulating fluid exits the radiator 20, passes through a tube or pipe that forms vertical header 34 and enters an opening 42 near the bottom of the transformer tank 10. The location of the sensor 30 provides access to insulating fluid that is in the coolest region of insulating fluid flow of the transformer 1 and does not interfere with the electronics of the sensor 30. In the embodiment of FIG. 3B, additional gasket connections and machined flanges are not needed, minimizing the possible points of insulating fluid leakage.

Figure 3C:
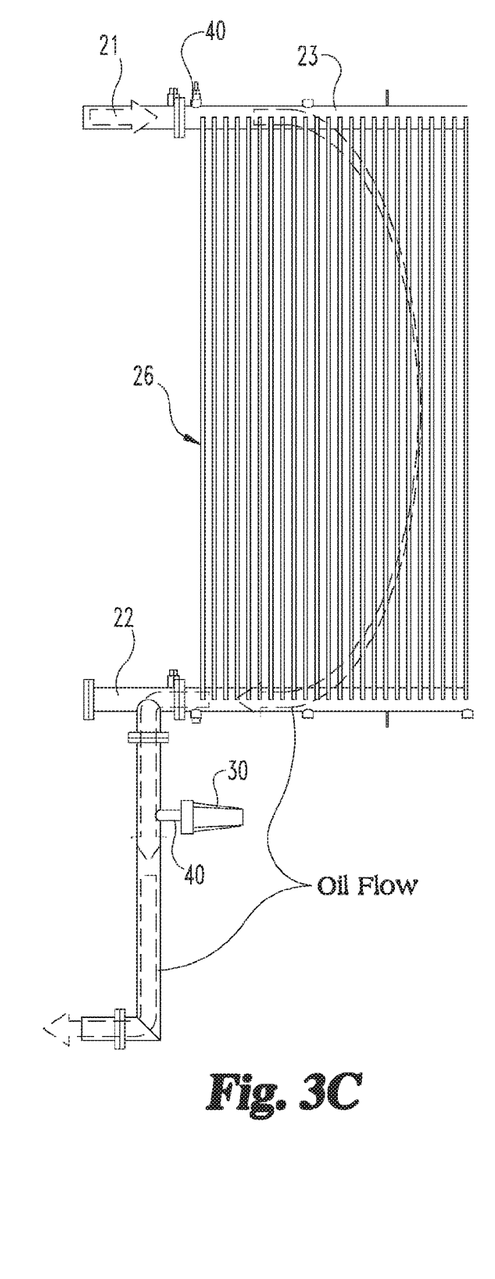
FIGS. 3C and 3D depict another embodiment vertically oriented header between the radiator and the transformer tank having a sensor
Figure 3D:
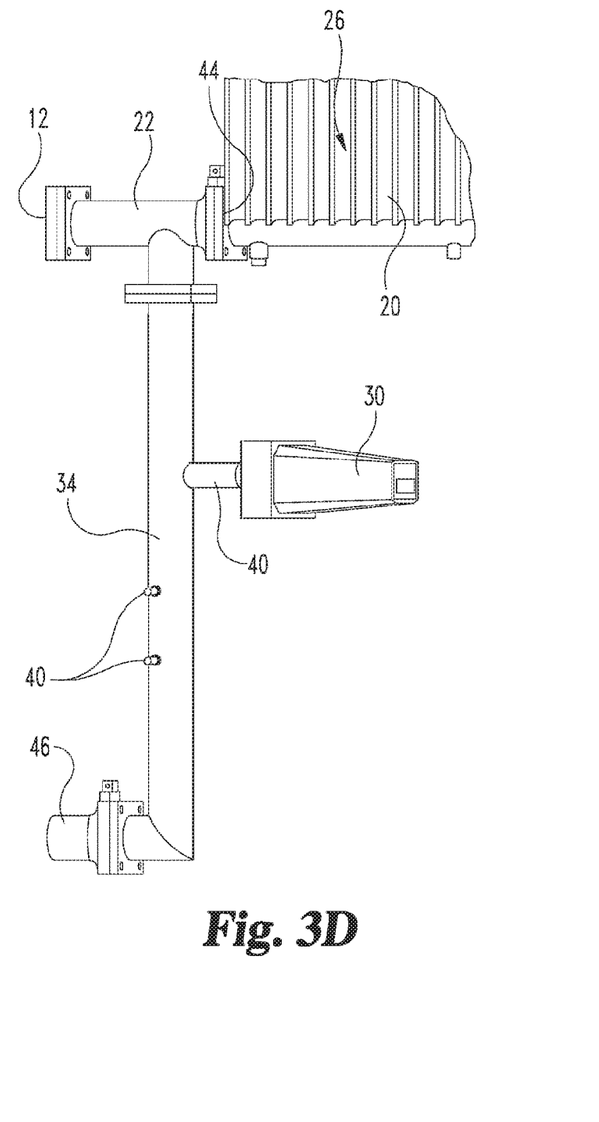

With reference to FIGS. 3C and 3D, a radiator 20 is shown in connection to the transformer tank through a first isolation valve 44, a second conduit 22, a header 34, and a second isolation valve 46. The first and second isolation valves 44, 46 allow insulating fluid flow to be turned off at the connection of radiator 20 with second conduit 22 and at the connection to the transformer tank 10 so that the header 34 can be removed. The sensor 30 has measurement access to the insulating fluid using a probe or measures the properties optically or acoustically through the port 40 of the header 34 or directly through header 34. The first and second isolation valves 44, 46 can be used to isolate the insulating fluid and remove the header 34 from connection between the radiator 20 and the transformer tank 10.

The port(s) 40 can be provided in at least one of the first conduit 21, second conduit 22 and the header 34 for measurement access by the sensor 30 in the example of FIGS. 3C and 3D. The sensor 30 may be any of the types previously mentioned. The location of the header 34 at or below a base of the radiator 20 and lower entrance point for the transfer of the insulating fluid from the radiator 20 to the transformer tank 10 near the isolation valve 44 contributes to the cooling of the insulating fluid. Such an arrangement allows for the addition of sensor 30 in-line with insulating fluid flow.

Figure 4:
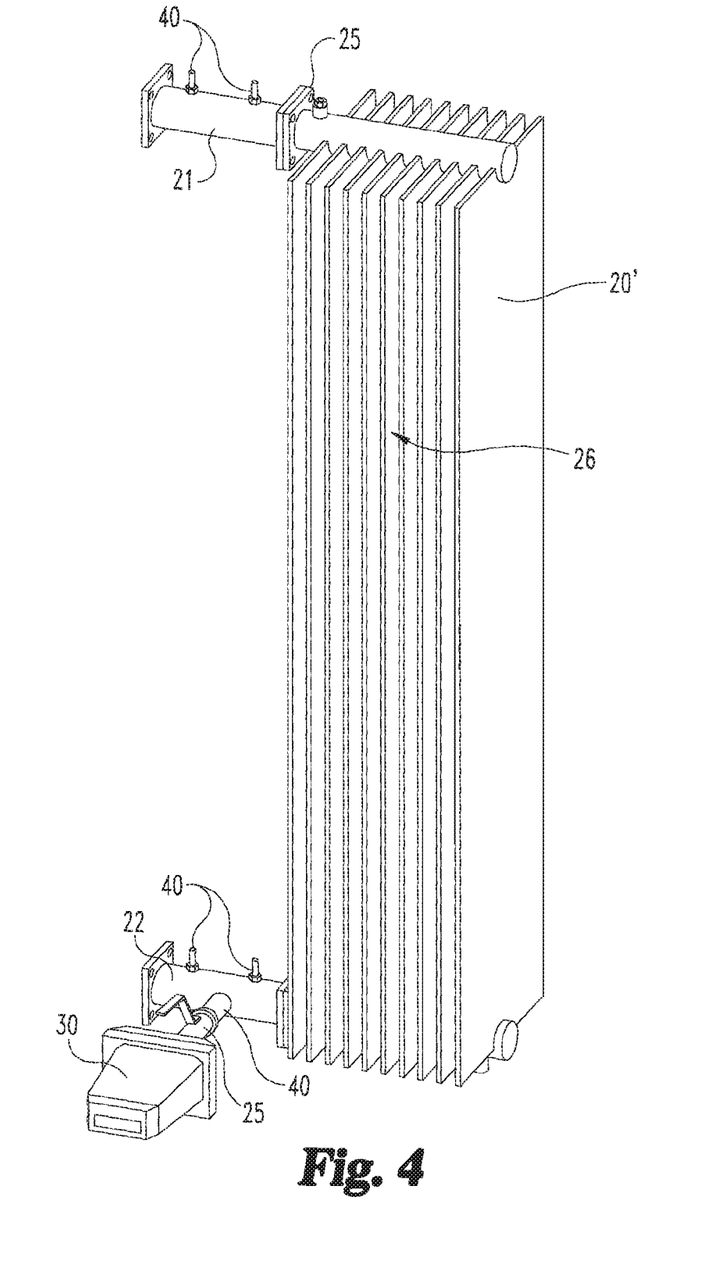
FIG. 4 depicts a radiator having sensors installed in a header between the valve and radiator.

Referring now to FIG. 4, a supplemental radiator 20' that can be used as a spare radiator is shown. The radiator 20' can be connected to an existing transformer radiator 20 or a new transformer radiator 20 with a first conduit 21 to produce the required insulating fluid flow and achieve the desired temperature range for sampling or measuring the insulating fluid. Ports 40 can be provided in a second conduit 22 at the bottom of supplemental radiator 20' to sense the insulating fluid properties. Due to the size of the supplemental radiator 20', the sensor 30 may be provided between the valve 25 and the second conduit 22 of radiator 20' without impacting the footprint of the radiator 20' or the transformer 10 to which the radiator 20' is connected.

Figure 5:
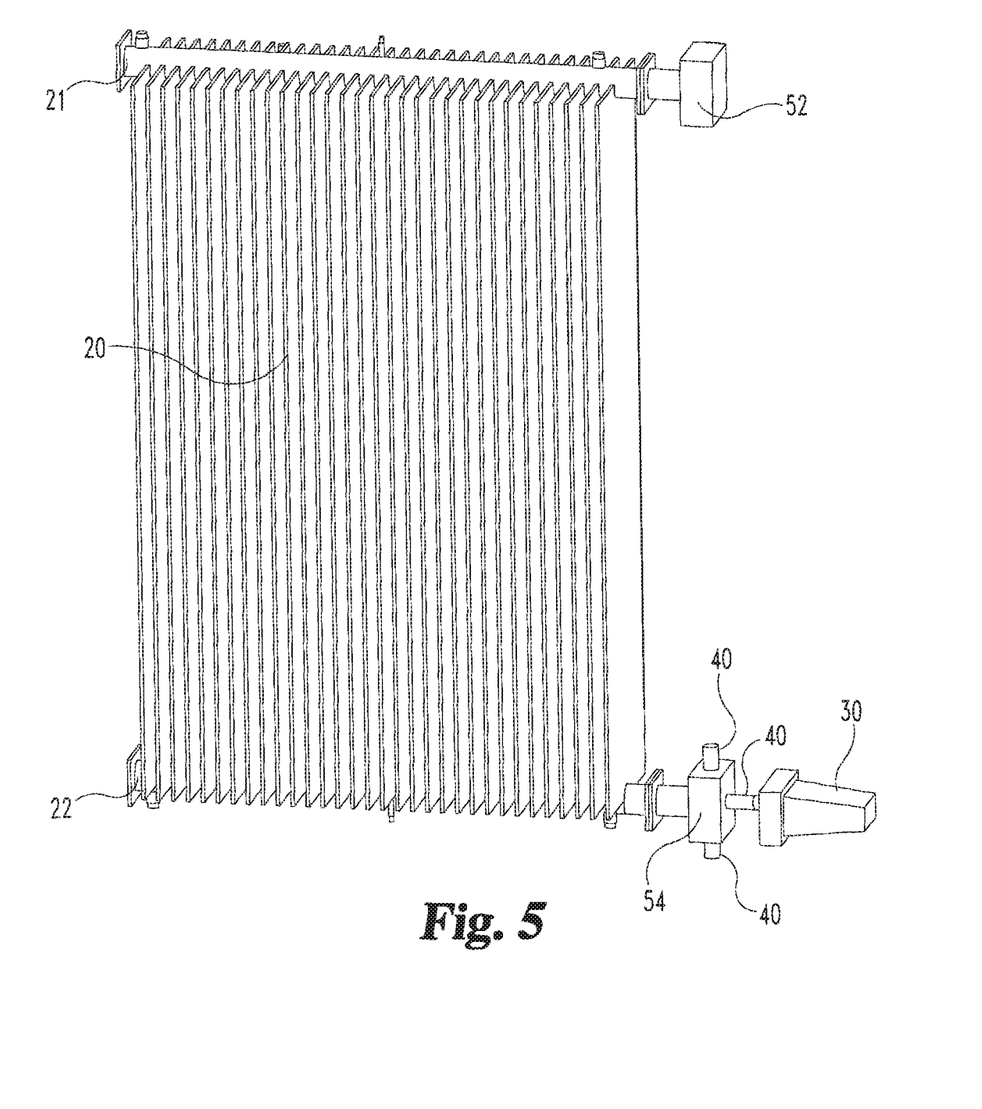
FIG. 5 depicts a radiator having a top and/or bottom header terminated with flanges and capable of interfacing with flanged sensor housings or flanged sensor ports.

Referring now to FIG. 5, the radiator 20 is shown having first and second flanged sensor housings 52, 54 and one or more ports 40 for accepting the sensor 30. The first flanged sensor housing 52 may be used to measure top oil temperature of the insulating fluid. The lower or bottom flanged sensor housing 54 can be connected to one or more sensors 30 at ports 40. The sensor housings 53, 54 can include a box shape to form a receptacle to accept and store insulating fluid and provide additional space for sensor elements to extend into the fluid from multiple ports 40.

Figure 6:
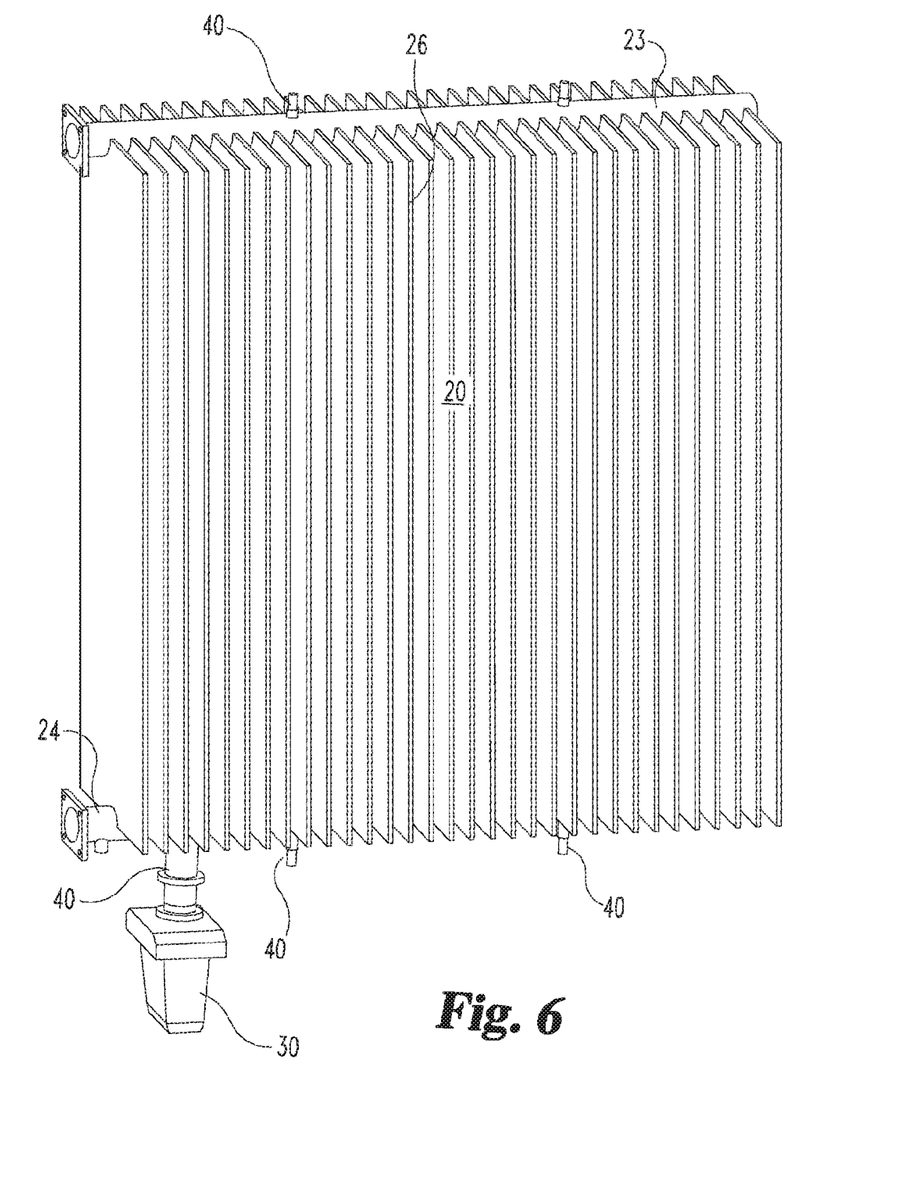
FIG. 6 depicts a radiator having the top and or/bottom headers provided with ports.

With reference now to FIG. 6, the radiator 20 includes first and second headers 23, 24 that are provided with multiple ports 40 for directly interfacing or connecting the sensor 30 with the insulating fluid. Direct measurement access to the insulating fluid within the first and second headers 23, 24 is thereby provided to one or more sensors 30. It should be understood that the port(s) 40 can be provided in any or all of the first and second conduits 21, 22, first and second horizontal headers 23, 24, the vertical header 34, and/or the first and second flanged sensor housings 52, 54 described herein. In addition, a valve can be connected at any of the ports 40 disclosed herein to facilitate removal and attachment of the sensor 30 thereto.

The sensor 30 can be mounted vertically or horizontally depending on the application. The sensor 30 provides wired or wireless communication to a readout of the sensor 30 or any system in an analog or digital manner. An example of a wired connection between the sensor 30 and processing unit provides an analog output of 4-20 mA representing one or multiple gasses dissolved in oil. Digital signals representing dissolved gas measurements may be provided from the sensor 30 through a wired connection or wirelessly using metallic pair, fiber optics, or another medium. Communication to other systems for monitoring the transformer are possible using MODBUS, DNP 3.0 and IEC61850 protocols. This same type of communication applies to all of the sensor types mentioned herein.

Various aspects of the present disclosure are contemplated. According to one aspect, a transformer includes tank for housing a core, at least one coil winding, an insulating fluid, and a radiator for receiving the insulating fluid from the tank. The radiator includes fins for cooling the insulating fluid and at least one of a conduit and a header for receiving the cooled insulating fluid from the radiator. The at least one of the conduit and the header includes a port for measurement access to the insulating fluid therein. A sensor is provided for measuring properties of the insulating fluid through the port.

In one embodiment, the sensor is selected from a group consisting of: a moisture sensor, a dissolved gas sensor, a resistance temperature detector, a photoacoustic sensor, a pressure sensor, a multi-gas detecting sensor, an oil level sensor, and any combination of the foregoing sensors. In another embodiment, the sensor is operable to communicate at least one measured value of the insulating fluid.

In yet another embodiment, the measured properties of the insulating fluid are selected from the group consisting of: a presence of at least one constituent in the insulating fluid, a constituent concentration of at least one constituent in the insulating fluid, a pressure of the insulating fluid, an insulating fluid temperature, an insulating fluid level, an interfacial tension, a power factor, a dielectric strength, a moisture content, an oxidation inhibitor content, an acidity, a color, and any combination of the foregoing.

In a further embodiment, a header is provided for receiving the cooled insulating fluid and further comprising first and second valves at respective ones of upstream and downstream ends of the header. In a refinement of this embodiment, the sensor is mounted to a port in the header. In a further refinement, a third valve is provided between the header and the sensor. In another refinement of this embodiment, at least a portion of the header is oriented horizontally along the radiator and the port is located on the portion that is oriented horizontally. In yet another refinement of this embodiment, at least a portion of the header is oriented vertically and extends downwardly from the radiator and the port is located on the portion that is oriented vertically.

According to another aspect, a transformer includes a tank for housing a core, at least one coil winding, an insulating fluid disposed within the tank, and a radiator for receiving the insulating fluid from the tank. The radiator includes fins for cooling the insulating fluid, a first header for receiving insulating fluid from the tank, and a second header for receiving cooled insulating fluid from the fins. The second header includes a port for measurement access to the insulating fluid therein and a sensor is provided for measuring properties of the insulating fluid through the port.

In one embodiment a sensor housing is attached to the second header for collection of insulating fluid for measurement by the sensor, the port is provided on the sensor housing, and the sensor is attached to the port. In another embodiment, at least a portion of the second header is oriented vertically and extends downwardly from the radiator and the port is located on the portion that is oriented vertically.

In yet another embodiment, at least a portion of the second header is oriented horizontally along the radiator and the port is located on the portion that is oriented horizontally. In a refinement of this embodiment, the second header is disposed below a base of the radiator.

In still another embodiment, a first conduit connects the first header to the tank and a second conduit connects the second header to the tank. In another embodiment, a first conduit connects the first header to the tank and second and third conduits connect the second header to an outlet of the radiator. In still another embodiment, the second header includes a plurality of ports for connection with sensors.

According to another aspect, a transformer includes a tank for housing a core, at least one coil winding, an insulating fluid disposed inside the tank, and a radiator for receiving the insulating fluid from the tank. The radiator includes fins for cooling the insulating fluid, a first header for receiving insulating fluid from the tank, and a second header for receiving cooled insulating fluid. A supplemental radiator is connected to the first radiator with a first conduit that receives the insulating fluid before the insulating fluid is cooled. The supplemental radiator includes fins for cooling the insulating fluid and a second conduit to receive cooled insulating fluid from the supplemental radiator. The second conduit includes at least one port for measurement access to the insulating fluid therein, and a sensor is provided for measuring properties of the insulating fluid through the port.

In one embodiment, a valve is provided between the second conduit and the sensor. In another embodiment, the first and second conduits each include a plurality of ports for connections with sensors.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application illustrates various embodiments, and while these embodiments have been described in some detail, it is not the intention of the applicant to restrict or in any way limit the scope of the appended claims to such detail. Additional advantages and modifications will readily appear to those skilled in the art. Therefore, the invention, in its broader aspects, is not limited to the specific details, the representative embodiments, and illustrative examples shown and described. Accordingly, departures may be made from such details without departing from the spirit or scope of the applicant's general inventive concept.

We claim:

1. A transformer, comprising:
   a tank for housing a core, at least one coil winding, and an insulating fluid;
   a radiator for receiving the insulating fluid from the tank, the radiator including fins for cooling the insulating fluid and a header for receiving the cooled insulating fluid from the radiator, wherein at least a portion of the header is oriented vertically and extends downwardly from the radiator and header includes a port located on the portion that is oriented vertically, the port for measurement access to the insulating fluid therein;
   first and second valves at respective ones of upstream and downstream ends of the header; and
   a sensor for measuring properties of the insulating fluid through the port.

2. The transformer according to claim 1, wherein the sensor is selected from a group consisting of: a moisture sensor, a dissolved gas sensor, a resistance temperature detector, a photoacoustic sensor, a pressure sensor, a multi-gas detecting sensor, an oil level sensor, and any combination of the foregoing sensors.

3. The transformer according to claim 1, wherein the measured properties of the insulating fluid are selected from the group consisting of: a presence of at least one constituent in the insulating fluid, a constituent concentration of at least one constituent in the insulating fluid, a pressure of the insulating fluid, an insulating fluid temperature, an insulating fluid level, an interfacial tension, a power factor, a dielectric strength, a moisture content, an oxidation inhibitor content, an acidity, a color, and any combination of the foregoing.

4. The transformer according to claim 1, wherein the sensor is operable to communicate at least one measured value of the insulating fluid.

5. The transformer according to claim 1, wherein the sensor is mounted to the port in the header.

6. The transformer according to claim 5, further comprising a third valve between the header and the sensor.

7. A transformer, comprising:
   a tank for housing a core, at least one coil winding, and an insulating fluid disposed within the tank;
   a radiator for receiving the insulating fluid from the tank, the radiator including fins for cooling the insulating fluid, a first header for receiving insulating fluid from the tank, a second header for receiving cooled insulating fluid from the fins, wherein at least a portion of the second header is oriented vertically and extends downwardly from the radiator and a port is located on the portion that is oriented vertically, the port for measurement access to the insulating fluid therein; and
   a sensor for measuring properties of the insulating fluid through the port.

8. The transformer according to claim 7, wherein a sensor housing is attached to the second header for collection of insulating fluid for measurement by the sensor, the port is provided on the sensor housing, and the sensor is attached to the port.

9. The transformer according to claim 8, wherein the second header is disposed below a base of the radiator.

10. The transformer according to claim 7, wherein a first conduit connects the first header to the tank and a second conduit connects the second header to the tank.

11. The transformer according to claim 7, wherein a first conduit connects the first header to the tank and second and third conduits connect the second header to an outlet of the radiator.

12. The transformer according to claim 7, wherein the second header includes a plurality of ports for connection with sensors.

13. A transformer comprising:
   a tank for housing a core, at least one coil winding, and an insulating fluid disposed inside the tank;
   a radiator for receiving the insulating fluid from the tank, the radiator including fins for cooling the insulating fluid, a first header for receiving insulating fluid from the tank, and a second header for receiving cooled insulating fluid,
   a supplemental radiator connected to the first radiator with a first conduit that receives the insulating fluid before the insulating fluid is cooled, the supplemental radiator including fins for cooling the insulating fluid and a second conduit to receive cooled insulating fluid from the supplemental radiator, wherein the second conduit includes at least one port for measurement access to the insulating fluid therein; and a sensor for measuring properties of the insulating fluid through the port.

14. The transformer of claim 13, further comprising a valve between the second conduit and the sensor.

15. The transformer of claim 13, wherein the first and second conduits each include a plurality of ports for connections with sensors.

* * * * *